(12) United States Patent
DeFraites

(10) Patent No.: US 8,366,996 B2
(45) Date of Patent: Feb. 5, 2013

(54) REFUSE DISINFECTION SYSTEM

(76) Inventor: Robert DeFraites, Kemer, LA (US)

( * ) Notice: Subject to any disclaimer, the term of this patent is extended or adjusted under 35 U.S.C. 154(b) by 344 days.

(21) Appl. No.: 12/807,276

(22) Filed: Sep. 1, 2010

(65) Prior Publication Data

US 2012/0051966 A1 Mar. 1, 2012

(51) Int. Cl.
*A61L 2/08* (2006.01)
*A61L 2/28* (2006.01)

(52) U.S. Cl. .................................. 422/26; 422/119
(58) Field of Classification Search .............. 422/26, 422/119
See application file for complete search history.

(56) References Cited

U.S. PATENT DOCUMENTS

| | | | |
|---|---|---|---|
| 4,249,929 | A | 2/1981 | Kneer |
| 4,316,871 | A | 2/1982 | De Fraites |
| 5,217,688 | A | 6/1993 | Von Lersner |
| 5,340,536 | A | 8/1994 | Datar et al. |
| 5,431,878 | A | 7/1995 | Vason et al. |
| 5,476,634 | A | 12/1995 | Bridges et al. |
| 6,190,618 | B1 | 2/2001 | Nelozuka et al. |
| 6,867,393 | B1 * | 3/2005 | Lewis ............... 219/401 |

* cited by examiner

*Primary Examiner* — Kevin Joyner
(74) *Attorney, Agent, or Firm* — Keaty Law Firm, LLC

(57) ABSTRACT

A system for disinfecting regulated refuse using steam disinfection used a refuse container where the regulated refuse is deposited. Temperature sensors are positioned below and above the refuse to detect the temperature of the disinfecting process, while a recording device operationally connected to the temperature sensors creates an identifying chart, which provides for identification of the time and temperature of processing, origin of the regulated refuse, as well as date and location of the processing.

8 Claims, 2 Drawing Sheets

REFUSE DISINFECTION SYSTEM

BACKGROUND OF THE INVENTION

This invention relates to a system for disinfecting garbage in a waste management industry, and more particularly, to a system for controlling the process of garbage disinfection using controlled heat application.

Waste processing for pathogen reduction has typically involved use of heat, cooling, pressurizing, and combinations of these to disinfect waste or place the waste in better condition for disinfection. In the marine industry, it has been commonplace in past years for the garbage, which accumulates on the ship and like refuse to be merely cast overboard. The dumping of such refuse or garbage at sea has now become illegal and seamen are required to dispose of their accumulated garbage by using onboard disinfection machines or at the port.

Historically, the U.S. has regulated garbage and refuse coming from foreign vessels. The purpose behind such regulations is to prevent the spread of dangerous plant diseases, insect pests, plant pests, and livestock and poultry diseases. Over time, there has been equipment and various methods developed to treat refuse, garbage and the like that has been quarantined due to governmental regulations. For example, the most common historical method to disinfect regulated garbage was through incineration or burning. However, this method has contributed significantly to the present problem of environmental pollution. As a result, various devices were developed to cause all refuse, garbage and other quarantined items to be disinfected, thus quickly and easily ridding the vessels, aircraft and other means of conveyance of the refuse problem.

In this country, refuse, garbage and the like is quarantined by the United States Department of Agriculture as soon as the garbage reaches the dock. Inspectors from the United States Department of Agriculture will normally require that the crewmen seal up the refuse or garbage in an approved container and, thereafter, demand that it be disposed of by suitable means to prevent the transfer of harmful disease or bacteria to the continental United States. One prior art method for dealing with this problem has been the incineration or burning of the garbage which itself contributes to environmental pollution.

Another method is taught in U.S. Pat. No. 4,316,871 issued on Feb. 23, 1982. The '871 patent discloses a closable chamber having a steam sparger supported above the bottom thereof, which sparger is covered by water placed in the bottom of the chamber during use thereof. While this device works satisfactory under many conditions, there is a need for a more controlled operation, where an operator is not required to guess at what point during the heating process the refuse can be considered fully disinfected. Additionally, there is a need for a system that would allow the waste management facility to demonstrate to the governmental agencies compliance with the waste treatment regulations.

SUMMARY OF THE INVENTION

It is, therefore, an object of the present invention to provide a system for disinfecting refuse that allows an operator to easily determine a point in time when the refuse disinfection process has been completed.

It is another object of the invention to provide a refuse disinfection system that can be used for disinfection of refuse, including garbage, which has been received under quarantine, from marine vessels, from aircraft or any other means of conveyance involved in foreign or interstate commerce.

It is another object of the invention to provide a system of refuse processing that generates a record for completed process for archival and/or reporting purposes.

These and other objects of the invention are achieved through a provision of a system for disinfecting refuse products, which comprises one or more refuse container, each having an inner chamber defined by a closed bottom, upwardly extending sidewalls and an open top selectively coverable with a lid. The inner chamber of each refuse container is configured for retaining refuse products therein during a disinfection process.

A sparger assembly is mounted adjacent the bottom of each refuse container and configured to admit steam into the inner chamber from an outside source of steam. The sparger assembly has an inlet conduit for connecting to the source of steam a regulating valve mounted in the inlet conduit and a continuous perforated sparger conduit secured near the bottom of each refuse container.

The system provides for the use of a pair of temperatures sensors" one sensor for positioning under the pile of refuse products deposited into the refuse container and the second—above the pile. The pair of temperature sensors prevent recording of unreliable temperature that exists only on the bottom or top of the garbage products.

The temperature sensors are operationally connected to a clocked recording device that has a chart for identifying each disinfecting process by the origin of the refuse products, the date, time and location of the disinfecting process, as well as the temperature maintained during the disinfecting process. The recording device can be connected to one or more refuse containers through the connection to the temperature sensors, thereby recording the identifying information for more than one process in one or more containers. The identifying chart generated by the recording device can be used for reporting to the governmental agencies or for the waste management company's archives.

An optional flexible cover, such as a tarpaulin cover, is provided for enveloping the refuse container and preventing escape of steam during the disinfecting process. The

BRIEF DESCRIPTION OF THE DRAWINGS

Reference will now be made to the drawings, wherein like parts are designated by like numerals, and wherein.

DETAIL DESCRIPTION OF THE INVENTION

Figure 1:
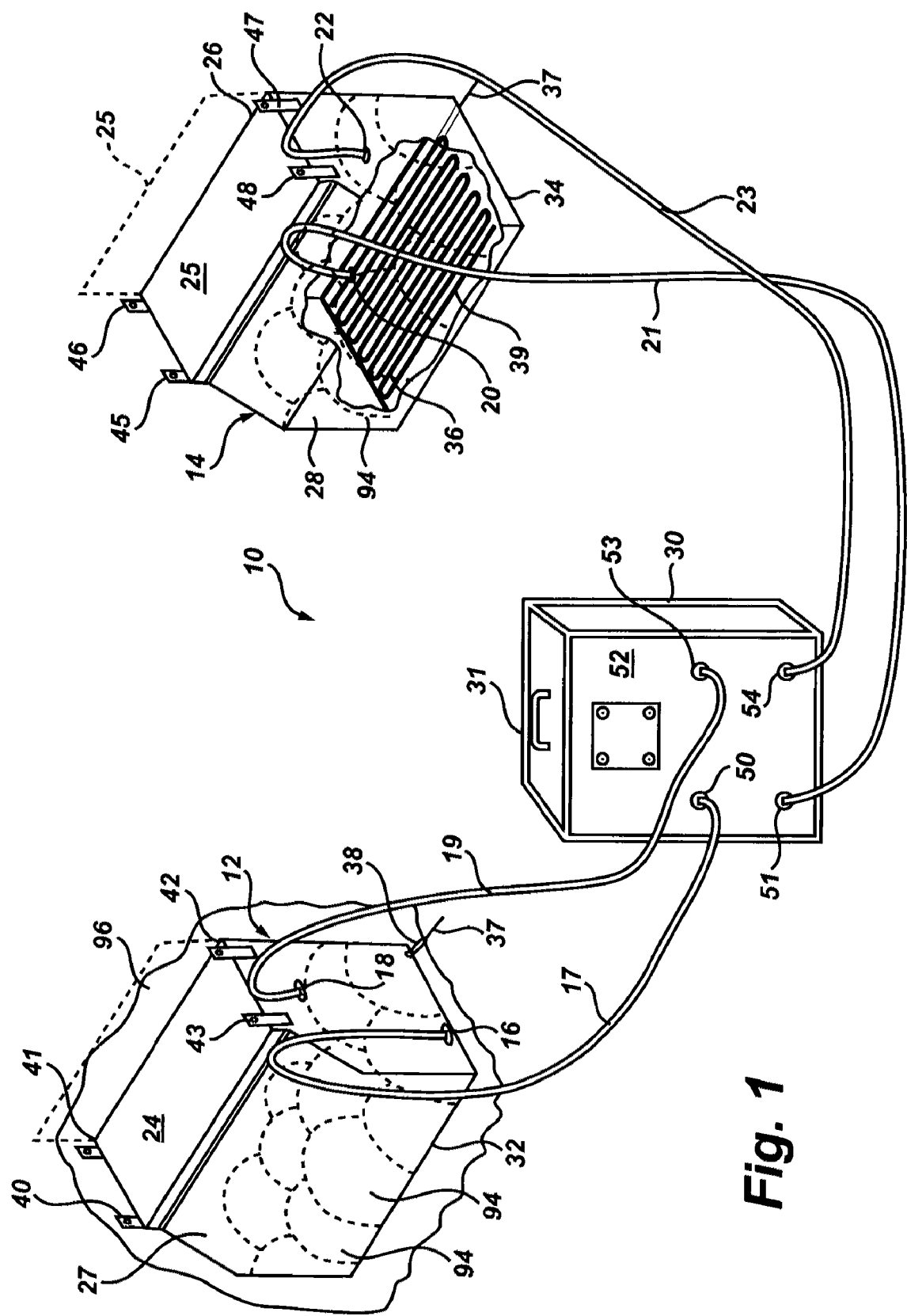
FIG. 1 is a schematic view of the system according to the present invention.

The system of the present invention is configured to process all types of the so-called "regulated garbage." According to the Code of Federal Regulations, 7 CFR §330.400 and 9 C.F.R. §94.5, "regulated garbage" comprises all waste material derived in whole or in part from fruits, vegetables, meats or other plant or animal (including poultry) material, and other refuse of any character whatsoever that has been associated with any material. The regulated garbage includes garbage that was on, generated on board, or removed from any means of conveyance during international or interstate movements. Further, regulated garbage includes food scraps, table refuse, galley refuse, food wrappers or packaging materials and other waste materials from stores, food preparation areas, passengers' or crews' quarters, dining rooms or any other areas on means of conveyance. Regulated garbage also is any meal or other foods available for consumption by passengers or crew on an aircraft, but was not actually consumed. Any garbage that comes into contact with regulated garbage becomes regulated garbage. This rule-defined "regulated garbage" is processed using the system of the present invention and becomes safe for disposal similar to domestic garbage in a municipal dumpsite.

Turning now to the drawings in more detail, numeral 10 designates the system of the present invention. The system 10 comprises one or more refuse processing containers 12 and 14, and temperature sensors 16, 18, 20, 22 operationally connected to a portable recording device 30. The temperature sensors 16 and 18 are connected to the recording device 30 by suitable cables 17 and 19, respectively. The temperature sensors 20, 22 are connected to the recording device 30 by suitable cables 21, 23, respectively.

Each refuse-processing container 12 and 14 comprises a hollow enclosure having a lid 24, 25, respectively hingedly secured to an open top along a hinge line 26. The lids 24, 25 pivot in relation to the hinge line to open and close the open tops of the containers 12 and 14. When the lids 24, 25 are in an open position (shown in phantom line in FIG. 1 with container 14) the operator can deposit garbage, refuse or the like into the inner chamber 27, 28 of the container 12 and 14.

Each container 12 and 14 has a closed bottom defined by plates 32 and 34, respectively, and closed sides defined by the upwardly extending sidewalls. The system of the present invention also comprises a sparger assembly that delivers heat into each of the refuse containers 12 and 14. Mounted adjacent the bottom plates 32 and 34 is a continuous sparger conduit 36, which forms a part of the sparger assembly. Although only one sparger conduit 36 is shown in FIG. 1 in relation to the container 14 it will be understood that a similar sparger conduit 36 is mounted in the container 12 adjacent the bottom plate 32.

The sparger conduit 36 has an inlet 37 provided with a valve 38 for controlling the inflow of steam into the containers 12 and 14 from an outside source of steam. The sparger conduit 30 can be, for example, in the form of a continuous pipe either coiled or folded in parallel sections, as shown in FIG. 1 inside the chambers 27, 28. The sparger conduit 36 has a cap-closed end opposite the inlet 37. The sparger conduit 36 is provided with a plurality of spaced-apart discharge openings 39 that allow introduction of steam into the containers 12 and 14.

The discharge openings 39 could be, for example, equally spaced a distance of six inches apart with each consecutive opening 39 being placed at an orientation of forty-five degrees (45.degree.) downwardly with respect to the horizontal plane while alternating in forwardly and rearwardly disposed positions. Thus, steam would be distributed to the left and to the right of the sparger conduit portions to provide an even distribution of steam within the inner chambers 27, 28 of the containers 12 and 14.

A plurality of lifting eyes 40, 41, 42, and 43 can be provided for attaching the container 12 to a crane or the like for elevating container 12 onto the deck of a vessel where a mass of garbage to be disinfected can be added thereto. A similar plurality of lifting eyes 45, 46, 47, and 48 can be secured to the top of the container 14 to allow maneuvering of the container 14 in the docks. A handle 31 is provided on the recording device 30 to allow the recording device to be transported from site-to-site and connected to different refuse containers.

The temperatures sensors 16 and 20 are positioned in the containers 12 and 14 prior to the addition of garbage to the containers. The connecting cables 17 and 21 are connected to the connection members 50, 51 on a back wall 52 of the recording device 30. The temperature sensors 18 and 22 are positioned in the containers 12 and 14 after the garbage has been deposited into the containers. The temperature sensors 20 and 22 are connected to the connection members 53, 54 on the back wall 52 of the recording device 30. By positioning the temperature sensors below and above the garbage in the containers 12 and 14, the operator ensures that there are "cold spots" during processing and the desired temperature of disinfection has bee reached in the pile of the refuse in the containers.

Figure 2:
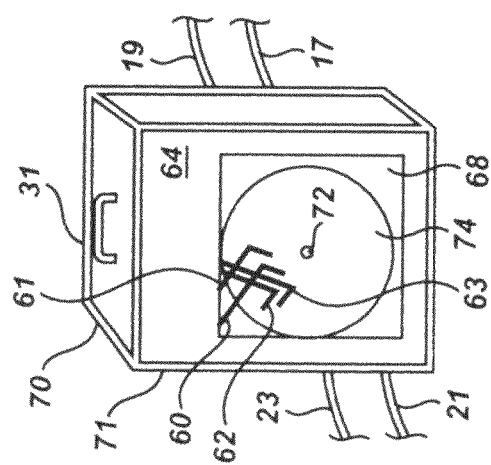
FIG. 2 is a front view of the recording device used in the system of this invention.

Each of the connection members 50-53 is operationally connected to a writing instrument, such as marking styluses 60-63 that extend to the front of the recording device 30. As can be seen in FIG. 2, the recording device 30 is provided with a transparent window 68 formed in a front wall 64. The front wall 64 is hinged to a sidewall 70, pivoting about a hinge 71 to allow the operator access the interior of the recording device 30.

The recording device 30 comprises a clock mechanism (not shown), which is mounted inside the recording device. The clock mechanism comprises a shaft 72, which is operationally connected to the clock mechanism and rotates similar to clock pin. A record chart 74 is detachably positioned on the shaft 72 and is configured to rotate with the shaft 72 in a clockwise direction.

Figure 3:
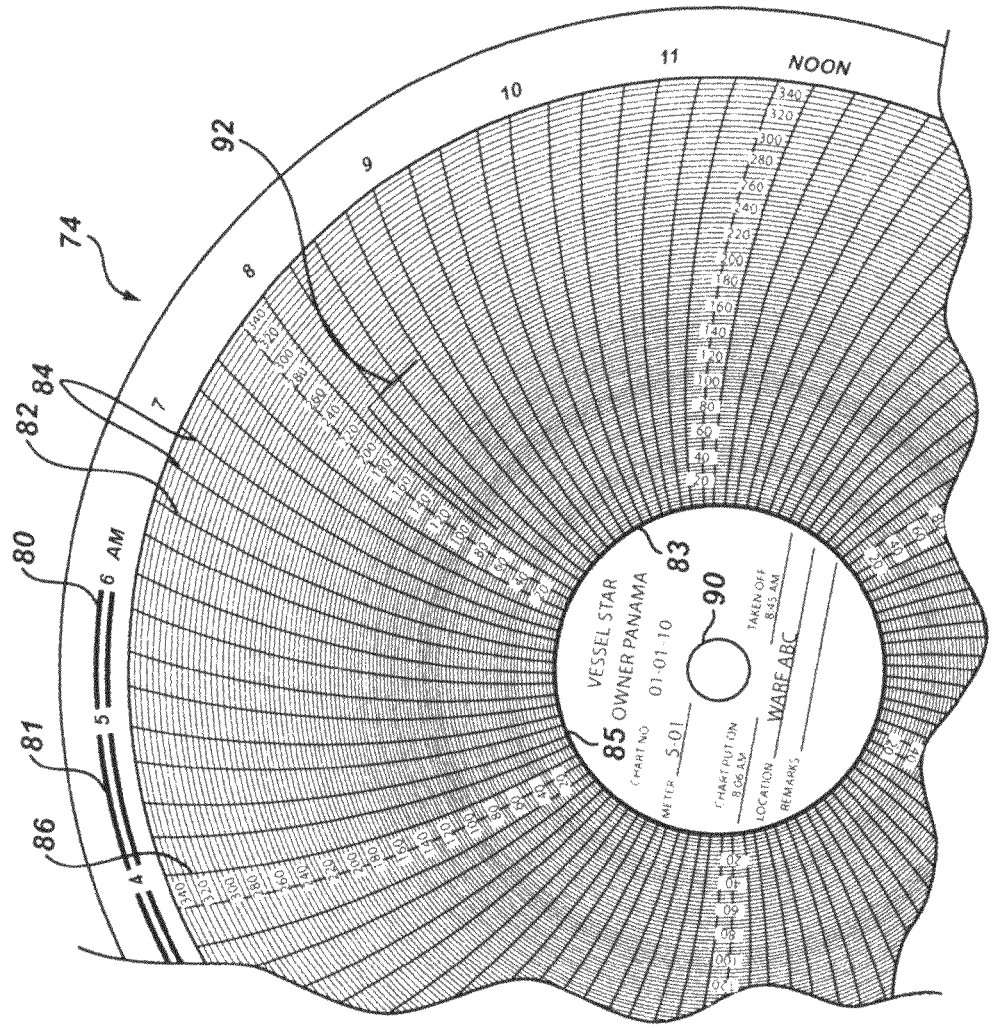
FIG. 3 is a detail view illustrating a chart generated by the recorder in use in the system of the present invention.

The front of the record chart is illustrated in FIG. 3. The chart 74 carries a plurality of indicia to facilitate recording of the time and temperature of processing by the refuse containers 12, 14. As can be seen in the drawing, the chart 74 comprises a time-designating indicia 80 imprinted about the outer circumference. The time-designating indicia divide the chart face into 24-hour segments 81, each segment 81 being divided into 15-minute portions 82 by curved radial lines 84. The timelines for each 15-minute portion 82 radiate from a center circle 83 toward the outer circumference of the time-designating indicia 80.

The indicia on the front face of the chart 74 further comprise circular temperature designations corresponding to the temperature values detected by the temperature sensors 16, 18, 20, and 22. The temperature circles start with the temperature line 85 corresponding to 0 degrees Fahrenheit, which is closest to the center circle 83, and extend to the temperature line 86, which is closer to the outer circumference of the chart 74 and corresponds to 340 degrees Fahrenheit. It is not anticipated that the high temperature of 340 degrees Fahrenheit will be required for processing of the garbage. However, the system of the present invention is capable of detecting and recording such temperature.

Imprinted within the center circle 83 is identifying indicia, such as the name of the vessel, the vessel owner, the chart number, the meter, the time when the process started (chart put in), the time when the chart was removed (taken off), the location of the processing, and a space for additional remarks.

An opening 90 allows mounting of the chart 74 on the clock shaft 72 to allow the marking styluses 60-63 to make a graph of the time of processing and the temperature reached inside the containers 12 and 14 during processing.

In operation, the operator positions the temperatures sensors 16 and 20 adjacent the bottom of the containers 12 and 14, making sure that the connecting cables 17 and 21 are connected to the recording device 30. The operator then fills the containers 12 and 14 with a disinfecting medium, such as water, to a level at least slightly above the sparger conduit 36, preferably to a level above the anticipated level of refuse in the containers. The operator then deposits garbage or refuse (schematically designated by numeral 94 in the drawings) into the containers 12 and 14, directly on top of the sparger conduit 36. An alternative step would be to first deposit the garbage into the container 12, 14 and then fill them with the disinfecting medium.

During the next step, the operator positions the temperature sensors 18 and 22 on top or above the refuse 94 and connects the cables 19 and 23 to the recording device 30. The operator then connects the inlet conduit 37 to a steam-generating machine (not shown) while the valves 38 are still closed. The operator then closes the lids 24, 25.

The operator then fills in the chart 74 with the name of the vessel, the vessel owner, the chart number, meter number and time when the disinfection process starts. In the example shown in FIG. 3, the identifying indicia has the name of the vessel (Star), owner of the vessel (Panama), chart number (01-01-10 corresponding to Jan. 1, 2010), meter number (S-01), location of the processing (Warf ABC) and the time when the garbage has been deposited into the disinfecting containers (8:06 am). The operator positions the chart 74 on the clock shaft 72 making sure that the writing styluses 60-63 are in contact with the imprinted face of the chart 74.

The recording device 30 begins rotation of the clock mechanism, as the operators admits steam through the inlet conduits 37 and valves 38 into the containers 12 and 14. Disinfecting the garbage is then started by admitting steam into the chambers 27, 28. The steam is distributed through the interior of the containers 12 and 14, while the temperature sensors detect the temperature of the garbage mass.

The writing styluses, being operationally connected to the temperature sensors 60-63 begin to graph the lines on the chart 74, the lines corresponding to the increase in temperature and the time. As shown in an illustrative example of FIG. 3, the temperature detected by one of the writing styluses rapidly increased to 220 degrees Fahrenheit shortly after 8:06 am, the time when the process started. This elevated temperature was sustained for about 45 minutes (indicia line 92), and the steam was turned off at about 8:45 am, when the chart was taken off the recording machine 30.

If desired, an optional flexible cover, for instance a tarpaulin cover 96 can be placed over the containers 12 and 14 to better seal the containers while the heating and disinfection process is taking place and to prevent escape of heat from the refuse containers 12 and 14. The cover 96 can be made from any moisture-impermeable material to thereby retain steam inside the containers.

The current regulations require that the refuse inside the container be steamed continuously for a minimum of thirty minutes at a temperature of at least 212 degrees Fahrenheit (100 degrees Celsius). The system of the present invention allows the waste management company to process the refuse and make a written record of the process. The recorded chart 74 can be archived, copied for submission to the EPA, or to a dumpsite as proof that the refuse has been properly disinfected for disposal in a municipal dump.

It is preferred that the container, hoses, sparger and other portion of the system coming into contact with the refuse be made from a non-corrosive material, such as metal or metal alloy. The chart 74 can be formed from paper or other inexpensive material. If desired, the system of this invention can be employed for two or more refuse containers, as long as the recording device is capable of recording the temperature and time of processing.

Many other changes and modifications can be made in the design of the present invention without departing from the spirit thereof. I, therefore, pray that my rights to the present invention be limited only by the scope of the appended claims.

I claim:

1. A method of disinfecting refuse products, comprising the steps:
   providing at least one refuse container having an inner chamber defined by a closed bottom, upwardly extending sidewalls, an open top, and a hinged lid for selectively covering the open top, said inner chamber being configured for retaining refuse products therein during a disinfecting process;
   providing a sparger assembly mounted adjacent the bottom of said at least one refuse container and configured to admit steam into the inner chamber;
   providing a first temperature sensor configured for detachable mounting in the inner chamber near the bottom of said at least one refuse container;
   depositing refuse products and a disinfecting medium into said inner chamber;
   providing a second temperature sensor configured for detachable mounting in the inner chamber at a level above the refuse products retained in the inner chamber; and
   providing a means for recording time and temperature of the disinfection process, said recording means being operationally connected to said first and said second temperature sensors;
   initiating the disinfecting process by admitting steam into the sparger assembly;
   recording temperature inside the inner chamber detected by the first and the second temperature sensors, while also recording time of the disinfecting process.

2. The method of claim 1, further comprising a step of identifying origin of the refuse products, time and temperature of the disinfecting process, and location of the disinfecting process.

3. The method of claim 2, further comprising a step of identifying a date of the disinfecting process.

4. The method of claim 1, further comprising a step of providing a flexible cover member and enveloping said at least one refuse container during the disinfecting process so as to prevent escape of heat from said at least one refuse container.

5. The method of claim 1, further comprising a step of connecting said means for recording to more than one refuse container and recording time and temperature of disinfecting process in more than one refuse container.

6. The method of claim 1, wherein said sparger assembly comprises an inlet conduit configured for connection to an outside source of steam and a valve mounted in said inlet conduit for selectively admitting steam into the inner chamber.

7. The method of claim 6, wherein the sparger assembly further comprises a sparger conduit mounted in the inner chamber and provided with a plurality of openings form delivering steam into the inner chamber.

8. The method of claim 1, wherein said means for recording comprises a portable recording device.

* * * * *